United States Patent

Müller et al.

[11] Patent Number: 6,037,443
[45] Date of Patent: Mar. 14, 2000

[54] THERMOPLASTIC ELASTOMERIC CARBON MONOXIDE/OLEFIN COPOLYMERS

[75] Inventors: Hans-Joachim Müller, Grünstadt; Hans Christoph Horn, Lambsheim; Roland Spahl, Lorsch; Bernhard Rieger; Adnan S. Abu-Surrah, both of Ulm, all of Germany

[73] Assignee: BASF Aktiengesellschaft, Ludwigshafen, Germany

[21] Appl. No.: 09/142,233

[22] PCT Filed: Mar. 6, 1997

[86] PCT No.: PCT/EP97/01129

§ 371 Date: Sep. 3, 1998

§ 102(e) Date: Sep. 3, 1998

[87] PCT Pub. No.: WO97/34943

PCT Pub. Date: Sep. 25, 1997

[30] Foreign Application Priority Data

Mar. 15, 1996 [DE] Germany ............ 196 10 358

[51] Int. Cl.[7] .................................................. C08G 67/02
[52] U.S. Cl. ................ 528/392; 524/706; 524/709; 524/714; 524/742; 524/765; 524/783; 524/785; 502/102; 502/150; 502/162; 502/171; 502/172; 502/208

[58] Field of Search ................ 528/392; 524/706, 524/709, 714, 742, 765, 783, 785; 502/102, 150, 162, 171, 172, 208

[56] References Cited

U.S. PATENT DOCUMENTS 5,352,767 10/1994 Chen .
5,384,393 1/1995 Hanna et al. .

FOREIGN PATENT DOCUMENTS 501 576 9/1992 European Pat. Off. .
516 238 12/1992 European Pat. Off. .

OTHER PUBLICATIONS

Makromol. Chem. 194, 2579–2603, (1993) Xu et al.
Macromolecules 1996, 29, 4806–4808, Abu–Surrah et al.

*Primary Examiner*—Samuel A. Acquah
*Attorney, Agent, or Firm*—Keil & Weinkauf

[57] ABSTRACT

Linear, thermoplastic, elastomneric copolymers of carbon monoxide and olefinically unsaturated compounds have an alternating sequence of repeating units and an average molecular weight Mw of the copolymers of from 80,000 to 1,200,000, binary, linear, alternating carbon monoxide/ethylene copolymers being excluded.

10 Claims, No Drawings

THERMOPLASTIC ELASTOMERIC CARBON MONOXIDE/OLEFIN COPOLYMERS

The present invention relates to linear, thermoplastic, elastomeric copolymers of carbon monoxide and olefinically unsaturated compounds having an alternating sequence of repeating units and an average molecular weight Mw of the copolymers of from 80,000 to 1,200,000, binary, linear, alternating carbon monoxide/ethylene copolymers being excluded.

The present invention furthermore relates to a process for the preparation of such copolymers, the use of the copolymers for the production of fibers, films and moldings, and the fibers, films and moldings comprising the copolymers and metal complexes (Ia) as defined hereafter.

Carbon monoxide/ethylene copolymers have recently attracted interest as engineering plastics for the production of articles having a relatively high melting point, for example gearwheels. As a rule, carbon monoxide copolymers with ethylene as comonotner are very hard and brittle and have little or no impact strength, making them unsuitable for many applications in which these properties are desirable.

U.S. Pat. No. 5,352,767 describes alternating, elastomeric copolymers of carbon monoxide and α-olefins, which copolymers were prepared using a catalyst system which contains cationic metal complexes of group VIIIB of the Periodic Table of Elements and activators based on primary and secondary alcohols.

However, the carbon monoxide/propylene, n-butene or n-hexene copolymers described herein have an average molecular weight Mw of only up to 50,000, which does not ensure thermoplastic elastomeric properties and moreover is too low for applications as engineering material.

Furthermore, a large excess of alcoholic activators is required for activating the polymerization catalysts.

It is an object of the present invention to provide copolymers of carbon monoxide and olefinically unsaturated compounds, which copolymers do not have said disadvantages or have them only to a minor extent and in particular have high average molecular weights Mw (80,000 or more) and both thermoplastic and elastomeric properties.

It is a further object of the present invention to provide a process for the preparation of these polymers which employs a catalyst which has polymerization activity without large amounts of activator, i.e. only up to 500 mole equivalents, based on the catalyst metal, or particularly preferably without any activator at all.

We have found that this object is achieved by linear, thermoplastic, elastomeric copolymers of carbon monoxide and olefinically unsaturated compounds having an alternating sequence of repeating units and an average molecular weight Mw of the copolymers of from 80,000 to 1,200,000, binary, linear, alternating carbon monoxide/ethylene copolymers being excluded.

We have also found a process for the preparation of linear, thermoplastic, elastomeric copolymers of carbon monoxide and olofinically unsaturated compounds having an alternating sequence of repeating units and an average molecular weight Mw of the copolymers of from 80,000 to 1,200,000, binary, linear, alternating carbon monoxide/ ethylene copolymers being excluded, by copolymerization of carbon monoxide with olefinically unsaturated compounds in a virtually alcohol-free or anhydrous polymerization medium in the presence of a catalyst whose active material is formed from A) a metal complex of the general formula (I)

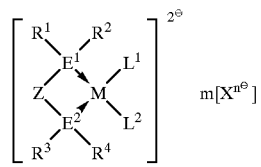

where:
M is a metal from group VIIIB of the Periodic Table of Elements,
$E^1$, $E^2$ are each an element from group VA of the Periodic Table of Elements,
Z is a bridging structural unit comprising one, two, three or four structural units of elements of group IVA, VA, VIA of the Periodic Table of Elements,
$R^1$ to $R^4$ are substituents selected from the group consisting of $C_1$- to $C_{20}$-organocarbon and $C_3$- to $C_{30}$-organosilicon radicals, where the radicals may contain one element or a plurality of elements from groups IVA, VA, VIA and VIIA of the Periodic Table of Elements,
$L^1$, $L^2$ are formally uncharged Lewis base ligands,
X is a monovalent or divalent anion,
m, n are each 1 or 2 and
m×n=2, and B) an activator component which contains a hydroxyl group in the molecule, from 0 to 500 mole equivalents, based on M in (I), of the activator component B) being used.

We have also found a process for the preparation of linear, thermoplastic, elastomeric copolymers of carbon monoxide and olefinically unsaturated compounds having an alternating sequence of repeating units and an average molecular weight Mw of the copolymers of from 80,000 to 1,200,000, binary, linear, alternating carbon monoxide/ethylene copolymers being excluded, by copolymerization of carbon monoxide with olefinically unsaturated compounds in a virtually alcohol-free or anhydrous polymerization medium in the presence of a catalyst whose active material is formed from a) a salt of a metal M of group VIIIB of the Periodic Table of Elements, b) a compound or a plurality of compounds selected from the group consisting of the protic acids and Lewis acids and c) a chelate compound of the general formula (II)

$$R^1R^2E^1-Z-E^2R^3R^4 \qquad (II)$$

where:
$E^1$, $E^2$ are each an element from group VA of the Periodic Table of Elements,
Z is a bridging structural unit comprising one, two, three or four structural units of elements of group IVA, VA or VIA of the Periodic Table of Elements and
$R^1$ to $R^4$ are substituents selected from the group consisting of $C_1$ to $C_{20}$-organocarbon and $C_3$- to $C_{30}$-organosilicon radicals, where the radicals may contain an element or a plurality of elements of group IVA, VA, VIA and VIIA of the Periodic Table of Elements, and B) an activator component which contains a hydroxyl group in the molecule, from 0 to 500 mole equivalents, based on M in (I), of the activator component B) being used,
and the use of the linear, thermoplastic, elastomeric copolymers defined at the outset for the production of fibers, films and moldings, the fibers, films and moldings comprising the linear, thermoplastic, elastomeric copolymers defined at the outset and metal complexes of the general formula (Ia)

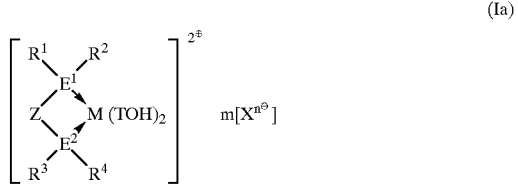

where:
- M is a metal of group VIIIB of the Periodic Table of Elements,
- $E^1$ and $E^2$ are each an element of group VA of the Periodic Table of Elements,
- Z is a bridging structural unit comprising one, two, three or four structural units of elements of group IVA, VA or VIA of the Periodic Table of Elements,
- $R^1$ to $R^4$ are substituents selected from the group consisting of $C_1$- to $C_{20}$-organocarbon and $C_3$- to $C_{30}$-organosilicbn radicals, where the radicals may contain an element or a plurality of elements IVA, VA, VIA and VIIA of the Periodic Table of Elements,
- TOH is a ligand in which T is hydrogen or a $C_1$- to $C_{15}$-organocarbon radical having a Lewis base group,
- X is a monovalent or divalent anion,
- m and n are each 1 or 2 and
- m×n=2.

The novel copolymers are composed of units which are based on the monomers carbon monoxide and an olefinically unsaturated compound or a plurality of olefinically unsaturated compounds, ethylene being excluded in binary copolymers since, on the basis of present knowledge, it gives only brittle materials.

The monomers are generally incorporated in an alternating manner in the copolymer.

Suitable olefinically unsaturated compounds are in principle all monomers of this class of compounds.

$C_3$- to $C_{20}$-alkenes or -alk-1-enes, for example propene, 1-butene, 2-butene, 1-pentene, 1-hexene, 1-octene, 1-nonene, 1-decene, 1-dodecene, 1-hexadecene, 1-octadecene, 1-eicocene, and mainly $C_3$- to $C_{10}$-alk-1-enes, such as propene, 1-butene, 1-hexene, 1-octene or 1-decene, are preferred in binary carbon monoxide copolymers. Very particularly preferred binary copolymers are carbon monoxide/propene copolymers.

In addition to the abovementioned ones, suitable olefinically unsaturated compounds are conjugated or isolated $C_4$- to $C_{20}$-dienes, for example 1,3-butadiene, 1,5-hexadiene, or norbornadiene, and furthermore $C_3$- to $C_{20}$-cycloolefins, such as cyclopentene, cyclohexene, norbornene and its derivatives.

Styrene may primarily be mentioned as an example of the suitable olefinically unsaturated aromatic monomers.

α,β-unsaturated carbonyl compounds, such as acrylic acid and methacrylic acid and derivatives thereof, including in particular the nitriles, the amides and the $C_1$–$C_6$-alkyl esters, for example ethyl acrylate, n-butyl acrylate, tert-butyl acrylate, methyl methacrylate and acrylonitrile, are furthermore important as polar, olefinically unsaturated compounds.

Further suitable olefinically unsaturated compounds are vinyl chloride, vinyl acetate, vinyl propionate, maleic anhydride and N-vinylpyrrolidone.

Suitable monomers for non-binary copolymers, in particular ternary copolymers, of carbon monoxide and olefinically unsaturated compounds are the abovementioned ones, but now including ethylene as a comonomer.

Carbon monoxide/ethylene/$C_3$- to $C_{20}$-alk-1-ene-terpolymers, such as carbon monoxide/ethylene/1-butene, carbon monoxide/ethylene/1-hexene, carbon monoxide/ethylene/1-octene and in particular carbon monoxide/ethylene/propene terpolymers are preferred. The content of structural units based on ethylene in the carbon monoxide/ethylene/$C_3$- to $C_{20}$-alk-1-ene terpolymer is in general from 0.1 to 70, preferably from 15 to 60, in particular from 20 to 50, mol %, based on the terpolymer. Particularly suitable terpolymers having these ethylene contents are carbon monoxide/ethylene/propene terpolymers.

The monomers are incorporated in the terpolymers and higher copolymers in general in an alternating carbon monoxide/comonotner(s) sequence.

The molar ratio of carbon monoxide to the sum of the structural units based on the olefinically unsaturated monomers in the novel binary and higher carbon monoxide copolymers is in general 1:1.

The novel copolymers are distinguished by their thermoplastic elastomeric properties in combination with relatively high molar mass.

The novel copolymers are, for example, soluble in dichloromethane at from 20 to 40° C., exhibit elastomeric behavior in the tensile test, measured using a Standard Universal Testing Machine Swick 1445 as described in the examples and generally have a crystallite melting point, measured by the Differential Scanning Calorimetry (DSC) method, of from 40 to 150° C.

The average molecular weight Mw of the novel carbon monoxide copolymers, measured by the gel permeation chromatography (GPC) method at 255C using Microstyragel (Waters) as column material and chloroform as solvent, against polystyrene standard, are in general from 80,000 to 1,200,000, preferably from 100,000 to 800,000, in particular from 100,000 to 600,000.

The molecular weight distribution Mw/Mn (weight average value/number average value) of the novel copolymers, measured by the gel permeation chromatography (GPC) method similarly to the above description, is in general from 1.5 to 3.5.

The polymerization for the preparation of the novel carbon monoxide copolymers can be carried out either batchwise or continuously in the presence of a polymerization catalyst comprising A) or a), b), and c) and optionally B).

Suitable polymerization catalysts are metal compounds of the eighth subgroup of the Periodic Table of Elements (VIIIB), which may be present as defined metal complexes (I) or (Ia), or may be formed in situ from a metal salt a) of the metals of group VIIIB of the Periodic Table of Elements, protic and/or Lewis acids b) and a chelate compound c) of the formula (II). If required, activators B) may be added to the metal compounds.

Suitable metals M are the metals of group VIIIB of the Periodic Table of Elements, i.e. namely the platinum metals, such as ruthenium, rhodium, osmium, iridium and platinum and very particularly palladium, in addition to iron, cobalt and nickel. The metals generally formally have a double positive charge in the complexes.

Suitable elements $E^1$ and $E^2$ of the chelate ligand, also referred to as chelate compound (II) below, or the elements of main group V of the Periodic Table of Elements (group VA), i.e. nitrogen, phosphorus, arsenic, antimony or bismuth.

Nitrogen and phosphorus are particularly suitable, especially phosphorus. The chelate ligand or the chelate compound (II) may contain different elements $E^1$ and $E^2$, for example nitrogen and phosphorus, very preferably contains identical elements $E^1$ and $E^2$ and in particular $E^1$ and $E^2$ are each phosphorus.

The bridging structural unit Z is a group of atoms which links the two elements $E^1$ and $E^2$ to one another. An atom or a plurality of atoms bonded to one another from group IVA, VA or VIA of the Periodic Table of Elements usually forms the bridge between $E^1$ and $E^2$. Possible free valences of these bridge atoms may be saturated in a variety of ways, for example by substitution with hydrogen, or elements from group IVA, VA, VIA or VIIA of the Periodic Table of Elements. The substituents may form ring structures with one another or with the bridge atom.

Suitable bridging structural units Z are those having one, two, three or four elements of group IVA of the Periodic Table of Elements, such as methylene (—$CH_2$-), 1,2-ethylene (—$CH_2$—$CH_2$—), 1,3-propylene (—$CH_2$—$CH_2$—$CH_2$—), 1,4-butylene, 1,3-disilapropylene (—$R^5R^6Si$—$CH_2$—$SiR^5R^6$—, where $R^5$ and $R^6$ are each $C_1$- to $C_{10}$-alkyl, $C_6$- to $C_{10}$-aryl), ethylidene ($CH_3(H)C$=), 2-propylidene (($CH_3)_2C$=), diphenylmethylene (($C_6H_5)_2C$=) or ortho-phenylene.

Examples of particularly suitable bridging structural units are 1,2-ethylene, 1,3-propylene and 1,4-butylene.

Suitable organocarbon radicals $R^1$ to $R^4$ are aliphatic as well as cycloaliphatic and aromatic ones of 1 to 20 carbon atoms, for example methyl, ethyl, 1-propyl, 1-butyl, 1-pentyl, 1-hexyl and 1-octyl. Linear arylalkyl groups, each having 1 to 10 carbon atoms in the alkyl radical and 6 to 20 carbon atoms in the aryl radical, such as benzyl, are also suitable. Examples of further radicals $R^1$ to $R^4$ are aryl, for example tolyl, anisyl and other substituted phenyl groups, in particular phenyl.

Suitable cycloaliphatic radicals are $C_3$- to $C_{10}$-monocyclic radicals, for example cyclopropyl, cyclobutyl, cyclopentyl and cyclohexyl, cyclohexyl being particularly preferred.

Suitable branched aliphatic radicals are $C_3$- to $C_{20}$-, preferably $C_3$- to $C_{12}$-alkyl, for example isopropyl, isobutyl, sec-butyl, neopentyl and tert-butyl.

Particularly suitable branch aliphatic radicals are tert-butyl, isopropyl and sec-butyl.

Alkyl groups having a branch further toward the outside are also suitable as substituents, e.g. isobutyl, 3 methylbutyl-2-yl and 4-methylpentyl.

Observations to date have shown that the chemical nature of the radicals $R^1$ to $R^4$ is not decisive, i.e. radicals may also contain atoms of group IVA, VA, VIA or VIIA of the Periodic Table of Elements, for example halogen, oxygen, sulfur, nitrogen or silicon, in the last-mentioned case, for example, bis(trimethylsilyl)methyl. Functional groups which are inert under the polymerization conditions are also suitable in this context.

Preferred heterosubstituents $R^1$ to $R^4$ are $C_3$- to $C_{30}$-organqsilicon radicals, i.e. tetravalent silicon atoms which on the one hand are bonded to $E^1$ or $E^2$ and whose remaining valences are saturated with three organocarbon radicals, the sum of the carbon atoms of these three radicals bonded to silicon being from 3 to 30. Examples are trimethylsilyl, tert-butyldimethylsilyl and triphenylsilyl, in particlar trimethylsilyl.

1,2-Bis(diphenylphosphino)ethane, 1,3-bis(diphenylphosphino)propane and 1,4-bis(diphenylphosphino)butane are preferably used as chelate ligands or chelate compounds (II).

Very particularly preferred compounds as the chelate ligand or chelate compound (II) are 1,3-bis(diphenylphosphino)propane and 1,4-bis(diphenylphosphino)butane.

Suitable formally uncharged ligands $L^1$ and $L^2$ are in general Lewis bases, i.e. compounds, preferably organic compounds or water, having at least one free electron pair, alkanols or phenols generally being unsuitable.

Suitable Lewis bases are those whose free electron pair or whose free electron pairs is or are present on a nitrogen or oxygen atom, i.e. nitrites, R—CN, ketones, ethers or preferably water.

Examples of suitable Lewis bases are $C_1$- to $C_{10}$-nitriles, such as acetonitrile, propionitrile and benzonitrile, $C_3$- to $C_{10}$-ketones, such as acetone and acetyl acetone, and $C_2$- to $C_{10}$-ethers, such as dimethyl ether, diethyl ether and tetrahydrofuran.

Particularly for catalysts which do not need an activator B), suitable ligands $L^1$ and $L^2$ in (I) or (Ia) are those of the formula (III)

$$T\text{—OH} \qquad \qquad (III).$$

In this formula, T is hydrogen or a $C_1$- to $C_{15}$-organocarbon radical provided with a Lewis base group. Suitable $C_1$ to $C_{15}$-organocarbon radicals T are, for example, linear or cyclic —($CH_2$)$_n$—units, where n is from 1 to 10, i.e. methylene, 1,2-ethylene, 1,3-propylene, 1,4-butylene, 1,5-pentylene, 1,6-hexylene, 1,7-heptylene, 1,8-octylene, 1,9-nonylene or 1,10-decylene.

Suitable Lewis base groups are ether, ester, ketone, amine, phosphane and in particular nitrile (—C≡N) or tertiary amines.

Suitable compounds T—OH are, for example, water or α,ω-hydroxynitriles, such as NC—($CH_2$)$_n$OH where n is from 1 to 10, or (2-hydroxymethyl)tetrahydrofuran and (2-hydroxymethyl)(N-organo)pyrrolidines (IIIa) or (2-hydroxymethyl)(N-organo)piperidines (IIIb)

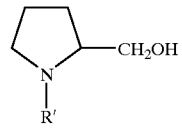

(IIIa)

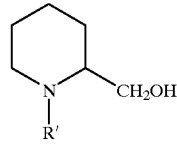

(IIIb)

where R' is $C_1$- to $C_{10}$-alkyl or $C_3$- to $C_{10}$-cycloalkyl, for example methyl, ethyl, n-propyl, isopropyl, n-butyl, isobutyl, sec-butyl, tert-butyl, cyclopentyl or cyclohexyl. R' may furthermore be $C_6$- to $C_{10}$-aryl, such as phenyl or naphthyl.

In general, the ligands T—OH, except for water, are bound to the metal M in (I) or (Ia) via the Lewis base group defined above.

Present knowledge indicates that it is advantageous if the anions X in (I) or (Ia) have as little nucleophilicity as possible, i.e. very little tendency to form a chemical bond with the central metal M.

Suitable anions X in (I) or (Ia) are, for example, perchlorate, sulfate, phosphate, nitrate and carboxylates, such as acetate, trifluoroacetate, trichloroacetate, propionate, oxalate, citrate and benzoate, and conjugated anions of organosulfonic acids, for example methylsulfonate, trifluoromethylsulfonate and para-toluenesulfonate, and furthermore tetrafluoroborate, tetraphenylborate, tetrakis (pentafluorophenyl)borate, hexafluorophosphate, hexafluoroarsenate and hexafluoroantimonate. Perchlorate, trifluoroacetate, sulfonates, such as methylsulfonate, trifluoromethylsulfonate and p-toluenesulfonate, tetrafluoroborate and hexafluorophosphate and in particular trifluoroacetate, perchlorate and p-toluenesulfonate are preferably used as anion X.

The substituents and indices of the metal complexes (Ia) have the meanings defined above for the metal complexes (I).

Examples of particularly suitable metal complexes (I) or (Ia) are bis-1,3(diphenylphosphino) propanepalladiumbisacetonitrile bis(tetrafluoroborate), bis-1,3(diphenylphosphino)propanepalladiumbisaquo bis (tetrafluoroborate), bis-1,4-(diphenylphosphino) butanepalladiumbisacetonitrile bis(tetrafluoroborate) and bis-1,4-(diphenylphosphino)butanepalladiumbisaquo bis (tetrafluoroborate).

The preparation of the metal complexes of the general formula (I) or (Ia) is carried out in general for processes known from literature, as described, for example, in Makromol. Chem. 194 (1993), 2579. Usually, tetrakis ligand metal complexes, such as tetrakis acetonitrilepalladium bistetrafluoroborate, can be reacted with the chelate compounds (II) and the ligands $L^1$, $L^2$ or TOH to give the metal comlexes (I) or (Ia). A preferred process for the preparation of aquo complexes (I) or (Ia) is the reaction of the chelate phosphane acetonitrile metal complexes with water. The reaction is carried out in general in a solvent, for example dichloromethane, acetonitrile or water, at from −78 to 40° C.

In the case of the in situ generation of the polymerization catalysts, the metals M are usually used in the divalent state in the from of their salts and are brought into contact with the chelate compound c) of the general formula (II) and the acids b). This may be effected before the catalytically active material thus obtainable comes into contact with the monomers and any further activator B), in general outside the polymerization reactor. Reaction of the individual components metal salts a), chelate compound c) of the general formula (II), acid b) and, if required, activator component B) can however also be carried out in the polymerization reactor, in the presence of the monomers.

Suitable salts of usually divalent metals M are halides, sulfates, phosphates, nitrates and carboxylates, such as acetates, propionates, oxalates, citrates and benzoates, and sulfonic acid salts, for example methylsulfonates, trifluoromethylsulfonate and para-toluenesulfonate. Carboxylates, sulfonic acid derivatives and in particular acetates are preferably used.

Particularly suitable catalyst components a) are palladium dicarboxylates, preferably palladium diacetate, palladium dipropionate, palladium bis(trifluoroacetate) and palladium oxalate, and palladium sulfonates, preferably palladium bis (trifluoromethanesulfonate), palladium bis (methanesulfonate) and palladium bis(p-toluenesulfonate), in particular palladium diacetate being used.

Lewis and protic acids and mixtures thereof may be used as catalyst components b).

Suitable protic acids b) are strong mineral acids, preferably having a small pKa value of less than 3, such as sulfuric acid and perchloric acid, and strong organic acids, for example trichloro- and trifluoroacetic acid, and, along with sulfonic acids, methanesulfonic acid, p-toluenesulfonic acid and benzenesulfonic acid.

Furthermore, the acid salts of strong acids with weak bases, for example ammonium salts of the abovementioned acids, are suitable.

Examples of suitable Lewis acids are halides of the elements of group IIIA of the Periodic Table of Elements, for example boron trifluoride, boron trichloride, aluminum trifluoride and aluminum trichloride, halides of elements of group VA of the Periodic Table of Elements, such as phosphorus pentafluoride and antimony pentafluoride, and halides of the metals of subgroup IVB of the Periodic Table of Elements, for example titanium tetrachloride or zirconium tetrachloride. Other suitable Lewis acids are organically substituted Lewis acids, for example tris (pentafluorophenyl)borane.

Preferably used Lewis acids are boron trifluoride, antimony pentafluoride and tris(pentafluorophenyl)borane.

Particularly preferred components b) are those which have a weakly coordinating conjugated anion, i.e. an anion which forms a weak bond to the central metal of the complex, such as tetrafluoroborate, hexafluorophosphate, perchlorate, trifluoroacetate, trifluoromethanesulfonate, p-tosylate and borates, e.g. pyrocate-cholatoborate.

In addition, suitable catalyst components a) and b) are those disclosed in general for systems with bisphosphenes in EP-A 501 576 and 516 238.

The catalyst systems contain, as component c), a chelate compound $R^1R^2E^1$—Z—$E^2R^3R^4$ (II), which were described above in the discussion of the metal complexes of (I).

The ratio of the catalyst components a), b) and c) to one another is chosen in general so that the molar ratio of the metal compound a) to the acid b) is from 0.01:1 to 100:1, preferably from 0.1:1 to 1:1, and the molar ratio of the metal compound a) to the component c) is from 0.01:1 to 10:1, preferably from 0.1:1 to 2:1.

The activator component B) is as a rule a chemical compound which contains at least one hydroxyl group in the molecule. It includes in particular $C_1$- to $C_{10}$-alcohols such as methanol, ethanol, n-propanol, isopropanol, n-butanol, isobutanol, sec-butanol, tert-butanol, n-hexanol, n-octanol, n-decanol, cyclohexanol, phenol and water. Methanol and/or water are preferably used as activator component B).

The molar ratio of activator component B) to metal M is from 0 to 500, preferably from 0 to 300. It has proven advantageous not to exceed the maximum ratio in the polymerization reaction, since otherwise the average molecular weight Mw of the resulting carbon monoxide copolymers may be too low.

It has unexpectedly been found that virtually no activator B) has to be added if the catalyst contains, as Lewis base ligands $L^1$ and $L^2$, those which contain a hydroxyl group in the molecule and which have been defined more exactly above by the general formula T—OH (III).

Pressures of from 100 to 500,000, preferably from 500 to 350,000, particularly from 1000 to 10,000 kPa and temperatures of from −50 to 400° C., preferably from 10 to 250° C., and in particular from 20 to 100° C., have proven suitable as reaction parameters for the preparation of the linear thermoplastic elastomeric copolymers from carbon monoxide and olefinically unsaturated compounds.

The polymerization reaction can be carried out in the gas phase, in suspension, in liquid and in supercritical monomers and in particular in solvents which are inert under the polymerization conditions.

The polymerization reaction can be carried out in virtually alcohol-free or anhydrous polymerization medium. This means that, except for any activator component B), no further amount of alcohol or water was or is added to the reaction mixture comprising monomers, catalyst and, if required, inert solvent or suspending agent.

Suitable inert solvents are those which contain no hydroxyl group in the molecule, i.e. ethers, such as diethyl ether, or tetrahydrofuran, aromatic solvents, such as benzene, toluene, ethylbenzene or chlorobenzene, and preferably chlorinated aliphatic hydrocarbons, such as dichloromethane, or 1,1,1-trichloromethane, and mixtures of the stated solvents.

Initially charging the catalyst in the inert solvent, if necessary subsequently adding the activator component B) and then adding the monomers and carrying out polymerization at from 20 to 100° C. and from 1000 to 10,000 kPa has proven a suitable polymerization process.

The novel carbon monoxide copolymers are suitable for the production of fibers, films and moldings, in particular those which are to have good impact strength. Furthermore, they may be used as blend components in plastics, in particular in those which are to have good impact strength.

EXAMPLES AND COMPARATIVE EXAMPLES 1 to 8

General Polymerization Conditions 100 ml of dichloromethane and 35 mg of palladium compound and, if required, the desired amount of the activator component B) were of propene (40 g, 0.95 mol) and carbon monoxide (5.0 g, 0.18 mol) was forced in at the chosen reaction temperature until the total pressure of 6000 kPa was reached.

In the case of the terpolymers (Experiments 7 and 8), 40 g of propene, 2 g of ethylene and 5 g of carbon monoxide (Experiment 7) or 40 g of propylene, 1 g of ethylene and 5 g of carbon monoxide (Experiment 8) were forced in until a total pressure of 6000 kPa was reached.

Polymerization was carried out at 25° C. for 30 hours. The temperature and the partial pressures of the monomers were kept constant during the entire reaction time. The polymerization was stopped by reducing the pressure to ambient pressure, methanol in hydrochloric acid was added to the reaction mixture, the mixture was filtered, the solvent was removed from the filtrate and the polymer was isolated. The experimental parameters are shown in Table 1 and the polymerization properties in Table 2.

Carrying Out the Tensile Tests:

The tensile tests were carried out with a Standard Universal Testing Machine Zwick 1445 tester.

For this purpose, sample films were produced by dissolving the olymers obtained in Experiments 1 to 8 in dichloromethane and vaporating the solvent. For the measurement, test strips (width 2 mm×thickness 0.5 mm×length 9 mm) were punched out.

The tensile tests were carried out at room temperature at a drawing speed of 10 mm/min. The distance was measured optically.

Measured curves which are characteristic for elastomers (comparative measurement with vulcanized polyisoprene) were obtained for the novel polymers.

TABLE 1

Experimental parameters (C after the experiment number represents a comparative experiment)

| No. | Complex, mg | Aktivator B), ml | Molar ratio activator B): complex | Activity, g of copolymer/(g of Pdxh)$^{-1}$ |
|---|---|---|---|---|
| 1 | (Ia), 35 | Methanol, 0.25 | 137:1 | 55.5 |
| 2C | (Ia), 35 | Methanol, 2.00 | 1096:1 | 62.9 |
| 3 | (Ia), 35 | Water, 0.001 | 1.23:1 | 10.4 |
| 4 | (Ia), 35 | Water, 0.25 | 307:1 | 51.9 |
| 5C | (Ia), 35 | Water, 2.00 | 2456:1 | 3.47 |
| 6 | (Ib), 35 | — | — | 27.0 |
| 7a) | (Ia), 35 | Water, 0.125 | 154:1 | 43.3 |
| 8a) | (Ia), 35 | Water, 0.125 | 154:1 | 21.7 |

(Ia) 1,3-bis(diphenylphosphino)propanePd(CH$_3$CN)$_2$ [BF$_4$]$_2$
(Ib) 1,3-bis(diphenylphosphino)propanePd(OH$_2$)$_2$ [BF$_4$]$_2$
a) Terpolymers of propylene, ethylene and carbon monoxide

TABLE 2

Polymer properties

| No. | Mw; Mw/Mn | Tg/Tm$^{c)}$ ° C. | Elastomer a) |
|---|---|---|---|
| 1 | 230000; 2.02 | 20.4/67.9; 100 | Yes |
| 2C | 36000; 2.35 | n.d. | No |
| 3 | 110000; 3.25 | 19.6/n.d. | Yes |
| 4 | 200000; 1.87 | 15.3/44.9; 90,2 | Yes |
| 5C | 13000; 1.21 | n.d. | No |
| 6 | 220000; 1.85 | 17.9/55.6 | Yes |
| 7b) | 411000; 2.30 | 9.8/46.9; 56,9 | Yes |
| 8b) | 589000; 3.02 | 21.7/44.8; 70.9 | Yes | a) Elastomer property was determined by means of the tensile test (see above).
b) Terpolymers of propylene, ethylene and carbon monoxide
c) Tg = glass transition temperature, Tm = melting point (e)

EXAMPLE 9

Preparation of bis(aquo)-{1,3-bis(diphenylphosphino) propane}-palladium(II) tetrafluoroborate complex:

A suspension of Pd(1,3-bis(diphenylphosphino)propane) (NCCH$_3$)$_2$ (BF$_4$)$_2$ (0.50 g, 0.65 mmol) in 50 ml of H$_2$O was stirred for 5 hours at room temperature. Thereafter, the solvent was decanted and the residue was washed with 100 ml of 1:1 diethyl ether/n-pentane. 0.46 g (98%) of diaqua complex remaining as a yellowish powder was dried in vacuo. Analysis for C$_{27}$H$_{30}$P$_2$O$_2$PdB$_2$F$_8$, calculated C,44.52, H, 4.15 found C,45.1, H, 4.29.; $^1$H-NMR (250 MHz, D$_6$-acetone, ppm): δ 7.92–7.43 (m, 20H, Harom.), 3.18(m, 4H), 2.39(m, 2H). IR (KBr, cm–1): ν(BF$_4$)=1062 (S, br).

We claim:

1. A linear, thermoplastic, elastomeric copolymer of carbon monoxide and olefinically unsaturated compounds having an alternating sequence of repeating units and an average molecular weight Mw of the copolymers of from 80,000 to 1,200,000, binary, linear, alternating carbon monoxide/ethylene copolymers being excluded.

2. A linear, thermoplastic, elastomeric copolymer as claimed in claim 1, the olefinically unsaturated compounds being C$_2$- to C$_{20}$-alk-1-enes.

3. A linear, thermoplastic, elastomeric copolymer as claimed in claim 1, comprising carbon monoxide, propene and ethylene.

4. A process for the preparation of linear, thermoplastic, elastomeric copolymers of carbon monoxide and olefinically unsaturated compounds having an alternating sequence of repeating units and an average molecular weight Mw of the copolymers of from 80,000 to 1,200,000, binary, linear, alternating carbon monoxide/ethylene copolymers being excluded, by copolymerization of carbon monoxide with olefinically unsaturated compounds in a virtually alcohol-free or anhydrous polymerization medium in the presence of a catalyst whose active material is formed from A) a metal complex of the general formula (I)

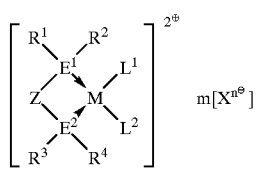
(I)

where:

M is a metal from group VIIIB of the Periodic Table of Elements, $E^1$, $E^2$ are each an element from group VA of the Periodic Table of Elements, Z is a bridging structural unit comprising one, two, three or four structural units of elements of group IVA, VA, VIA of the Periodic Table of Elements, $R^1$ to $R^4$ are substituents selected from the group consisting of $C_1$- to $C_{20}$-organocarbon and $C_3$- to $C_{30}$-organosilicon radicals, where the radicals may contain one element or a plurality of elements from groups IVA, VA, VIA and VIIA of the Periodic Table of Elements, $L^1$, $L^2$ are formally uncharged Lewis base ligands, X is a monovalent or divalent anion, m, n are each 1 or 2 and m×n=2, and B) an activator component which contains a hydroxyl group in the molecule, wherein from 0 to 500 mole equivalents, based on M in (I), of the activator component B) are used.

5. A process for the preparation of linear, thermoplastic, elastomeric copolymers of carbon monoxide and olefinically unsaturated compounds having an alternating sequence of repeating units and an average molecular weight Mw of the copolymers of from 80,000 to 1,200,000, binary, linear, alternating carbon 40 monoxide/ethylene copolymers being excluded, by copolymerization of carbon monoxide with olefinically unsaturated compounds in a virtually alcohol-free or anhydrous polymerization medium in the presence of a catalyst whose active material is formed from a salt of a metal M of group VIIIB of the Periodic Table of Elements, b) a compound or a plurality of compounds selected from the group consisting of the protic acids and Lewis acids and c) a chelate compound of the general formula (II)

$$R^1R^2E^1\text{—}Z\text{—}E^2R^3R^4 \qquad (II)$$

where:

$E^1$, $E^2$ are each an element from group VA of the Periodic Table of Elements, Z is a bridging structural unit comprising one, two, three or four structural units of elements of group IVA, VA or VIA of the Periodic Table of Elements and $R^1$ to $R^4$ are substituents selected from the group consisting of $C_1$- to $C_{20}$-organocarbon and $C_3$- to $C_{30}$-organosilicon radicals, where the radicals may contain an element or a plurality of elements of group IVA, VA, VIA and VIIA of the Periodic Table of Elements, and B) an activator component which contains a hydroxyl group in the molecule, wherein from 0 to 500 mole equivalents, based on M in (I), of the activator component B) are used.

6. The process as claimed in claim 4, wherein $L^1$ and $L^2$ in (I) are ligands of the general formula T—OH (III) where T=is hydrogen or $C_1$- to $C_{15}$-organocarbon radical having a Lewis acid group, and no activator component B) is used.

7. The process as claimed in claim 4, wherein $E^1$ and $E^2$ are each phosphorus.

8. A fiber, film or molding comprising a linear, thermoplastic, elastomeric copolymer as claimed in claim 1.

9. A metal complex of the general formula (Ia)

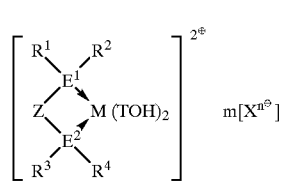
(Ia)

where:

M is a metal of group VIIIB of the Periodic Table of Elements, $E^1$ and $E^2$ are each an element of group VA of the Periodic Table of Elements, Z is a bridging structural unit comprising one, two, three or four structural units of elements of group IVA, VA or VIA of the Periodic Table of Elements, $R^1$ to $R^4$ are substituents selected from the group consisting of $C_1$- to $C_{20}$-organocarbon and $C_3$- to $C_{30}$-organosilicon radicals, where the radicals may contain an element or a plurality of elements IVA, VA, VIA and VIIA of the Periodic Table of Elements, TOH is a ligand in which T is hydrogen or a $C_1$- to $C_{15}$-organocarbon radical having a Lewis base group, X is a monovalent or divalent anion, m and n are each 1 or 2 and m×n=2.

10. A process comprising producing fibers, films or moldings using a linear, thermoplastic, elastomeric copolymer as claimed in claim 1.

* * * * *

UNITED STATES PATENT AND TRADEMARK OFFICE
CERTIFICATE OF CORRECTION

PATENT NO. : 6,037,443
DATED : March 14, 2000
INVENTOR(S) : Muller et al.

It is certified that error appears in the above-identified patent and that said Letters Patent is hereby corrected as shown below: Title page, item [57], In the Abstract:

In the first line, change "elastomneric" to --elastometric--.

Signed and Sealed this

Sixth Day of February, 2001

Attest:

Q. TODD DICKINSON

Attesting Officer
Director of Patents and Trademarks

UNITED STATES PATENT AND TRADEMARK OFFICE
CERTIFICATE OF CORRECTION

PATENT NO. : 6,037,443
DATED : March 14, 2000
INVENTOR(S) : Mueller et al.

It is certified that error appears in the above-identified patent and that said Letters Patent is hereby corrected as shown below:

On the title page, Item [57], Abstract

On the first line, change "elastomneric" to --elastomeric--.

This certificate supercedes Certificate of Correction issued February 6, 2001.

Signed and Sealed this

First Day of May, 2001

Attest:

NICHOLAS P. GODICI

Attesting Officer

Acting Director of the United States Patent and Trademark Office